United States Patent [19]

Furch et al.

[11] Patent Number: 5,585,389
[45] Date of Patent: Dec. 17, 1996

[54] AMIDRAZONES AND THEIR USE AS INSECTICIDAL AND ACARICIDAL AGENTS

[75] Inventors: Joseph A. Furch, Lawrenceville, N.J.; David G. Kuhn; David A. Hunt, both of Newtown, Pa.

[73] Assignee: American Cyanamid Company, Madison, N.J.

[21] Appl. No.: 431,227

[22] Filed: Apr. 28, 1995

Related U.S. Application Data

[62] Division of Ser. No. 998,105, Dec. 29, 1992, Pat. No. 5,420,165.

[51] Int. Cl.$^6$ .................................................. A01N 43/40
[52] U.S. Cl. .................. 514/349; 514/332; 514/334; 514/335; 514/345; 514/348; 514/353
[58] Field of Search .................. 514/353, 349, 514/332, 334, 335, 345, 348

[56] References Cited

U.S. PATENT DOCUMENTS

| | | | |
|---|---|---|---|
| 3,214,334 | 10/1965 | Freund et al. | 167/30 |
| 3,505,403 | 4/1970 | Viehe | 260/564 |
| 3,745,215 | 7/1973 | Kaugars | 424/327 |
| 3,786,094 | 1/1974 | Perronnett et al. | 260/564 R |
| 3,879,542 | 4/1975 | Kaugars | 424/327 |
| 3,917,849 | 11/1975 | Boesch | 424/327 |
| 3,935,315 | 1/1976 | Boesch | 424/327 |
| 4,925,864 | 5/1990 | Inamoria et al. | 514/383 |

FOREIGN PATENT DOCUMENTS

| | | |
|---|---|---|
| 0325983 | 8/1989 | European Pat. Off. |
| 2184974 | 4/1972 | France |
| 4200591A1 | 7/1993 | Germany |
| 214541 | 9/1966 | U.S.S.R. |
| 736473 | 9/1955 | United Kingdom |

OTHER PUBLICATIONS

R. G. Dubenko, Organic Chemistry Inst. Acad. Science UKR. S.S.R., Oct., 1968 (English Language Abstract).
Boehringer Mannheim GmbH., Dt-2,030,218-Q (English Language Abstract).
Smith, et al., "Amidrazones. II. Tautomerism and Alkylation Studies," J. Org. Chem. 38(7):1344-1348 (1973).
Chapelle et al., "Recherches sur les enehydrazines," Bull. de la Societe Chimique de France, o. 1, 1971, pp. 283-286.
Cunningham et al., "Acid, Base, and Uncatalysed Isomerisation of Z-to E-Amidine. A Machanistic Study," J. Chem. Soc. Perkin trans. II 1986, pp. 537-541.
Chemical Abstracts, vol. 92, No. 21, May 26, 1980, Abstract No. 180607j, Khrustaleu et al.

*Primary Examiner*—Allen J. Robinson
*Attorney, Agent, or Firm*—John W. Hogan, Jr.

[57] ABSTRACT

There are provided substituted acid amide, arylhydrazone compounds (amidrazones) of formula I

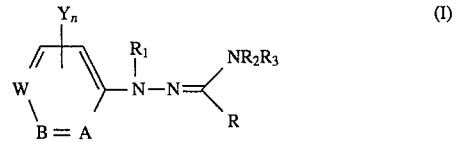

the use thereof for the control of insect and acarid pests and methods and compositions for the protection of crops from the damage and loss caused by said pests.

9 Claims, No Drawings

AMIDRAZONES AND THEIR USE AS INSECTICIDAL AND ACARICIDAL AGENTS

This is a divisional of application Ser. No. 07/998,105 filed on Dec. 29, 1992 now U.S. Pat. No. 5,420,165.

BACKGROUND OF THE INVENTION

Certain insect and acarid pests are harmful and cause enormous losses annually and animal health. It is an object of this invention to provide substituted acid amide, N-arylhydrazone compounds (amidrazones) which are effective agents for the control of pestiferous insects and acarina.

It is another object of this invention to provide a method for the protection of important agronomic crops from the harmful and damaging effects caused by insect and acarid pests.

It is a further object of this invention to provide insecticidal and acaricidal compositions.

SUMMARY OF THE INVENTION

The present invention provides a method for the control of insects or acarina which comprises contacting said insects or acarina or their food supply, breeding ground or habitat with an insecticidally effective amount of an amidrazone compound of formula I $$\begin{array}{c} Y_n \\ \diagup\!\!\!\!\diagdown \\ W \quad \quad R_1 \quad NR_2R_3 \\ \diagdown \quad \;\;|\quad\;\;\diagup \\ \quad\quad\quad N{-}N{=} \\ B{=}A \quad\quad\quad R \end{array} \quad (I)$$

wherein

A is C-$R_4$ or N;
B is C-$R_5$ or N;
W is C-$R_6$ or N with the proviso that one of A, B or W must be other than N;
Y is hydrogen, halogen, CN, $NO_2$, $C_1$-$C_6$-alkyl, $C_1$-$C_6$-haloalkyl, $C_1$-$C_6$alkoxy or $C_1$-$C_6$haloalkoxy;
n is an integer of 0, 1 or 2;
R is hydrogen, $C_1$-$C_{10}$alkyl optionally substituted with one or more halogens, $C_3$-$C_6$cycloalkyl, $C_1$-$C_4$alkoxy, $C_1$-$C_4$haloalkoxy, ($C_1$-$C_4$haloalkyl)$SO_x$, phenyl optionally substituted with one to three halogen, $C_1$-$C_4$alkyl, $C_1$-$C_4$haloalkyl, $C_1$-$C_4$alkyl)$SO_x$, ($C_1$-$C_4$haloalkyl)$SO_x$, $NO_2$ or CN groups, or phenoxy optionally substituted with one to three halogen, $C_1$-$C_4$alkyl, $C_1$-$C_4$haloalkyl, $C_1$-$C_4$alkoxy, $C_1$-$C_4$-haloalkoxy, ($C_1$-$C_4$alkyl)$SO_x$, ($C_1$-$C_4$-haloalkyl)$SO_x$, $NO_2$ or CN groups, $C_3$-$C_{12}$ cycloalkyl optionally substituted with one or more halogens, $C_1$-$C_6$alkyl, $C_1$-$C_6$haloalkyl, $C_1$-$C_4$alkoxy, $C_1$-$C_4$-haloalkoxy, ($C_1$-$C_4$alkyl)$SO_x$, ($C_1$-$C_4$haloalkyl)$SO_x$, phenyl optionally substituted with one to three halogen, $C_1$-$C_4$alkyl $C_1$-$C_4$haloalkyl, $C_1$-$C_4$alkoxy, $C_1$-$C_4$haloalkoxy, $NO_2$ or CN groups, or phenoxy optionally substituted with one to three halogen, $C_1$-$C_4$alkyl, $C_1$-$C_4$haloalkyl, $C_1$-$C_4$alkoxy, $C_1$-$C_4$haloalkoxy, $NO_2$ or CN groups, or phenyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups;

$R_1$ is hydrogen or $C_1$-$C_4$alkyl;
$R_2$ and $R_3$ are each independently hydrogen, $C_1$-$C_{10}$ alkyl optionally substituted with one or more halogen, hydroxy, $C_1$-$C_4$alkoxy, ($C_1$-$C_4$alkyl)$SO_x$, $CONR_7R_8$, $CO_2R_9$, $R_{10}$, $R_{11}$, $C_3$-$C_6$cycloalkyl optionally substituted with one to three halogen $C_1$-$C_4$alkyl, $C_1$-$C_4$haloalkyl, $C_1$-$C_4$alkoxy, $C_1$-$C_4$haloalkoxy, $NO_2$ or CN groups, phenyl optionally substituted with one or more halogen, $C_1$-$C_4$alkyl, $C_1$-$C_4$haloalkyl, $C_1$-$C_4$alkoxy, $C_1$-$C_4$haloalkoxy, $CO_2$ or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, $C_3$-$C_{10}$alkenyl optionally substituted with one or more halogen, hydroxy, $C_1$-$C_4$alkoxy, ($C_1$-$C_4$alkyl)$SO_x$, $CONR_7R_8$, $CO_2R_9$, $R_{10}$, $R_{11}$, $C_3$-$C_6$cycloalkyl optionally substituted with one to three halogen, $C_1$-$C_4$alkyl, $C_1$-$C_4$haloalkyl, $C_1$-$C_4$alkoxy, $C_1$-$C_4$haloalkoxy, $NO_2$ or CN groups, phenyl optionally substituted with one or more halogen, $C_1$-$C_4$alkyl, $C_1$-$C_4$haloalkyl, $C_1$-$C_4$alkoxy, $C_1$-$C_4$haloalkoxy, $CO_2$ or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, $C_3$-$C_{10}$alkenyl optionally substituted with one or more halogen, hydroxy, $C_1$-$C_4$alkoxy, ($C_1$-$C_4$alkyl)$SO_x$, $CONR_7R_8$, $CO_2R_9$, $R_{10}$, $R_{11}$, $C_3$-$C_6$cycloalkyl optionally substituted with one to three halogen, $C_1$-$C_4$alkyl, $C_1$-$C_4$haloalkyl, $C_1$-$C_4$alkoxy, $C_1$-$C_4$haloalkoxy, $NO_2$ or CN groups, phenyl optionally substituted with one or more halogen, $C_1$-$C_4$alkyl $C_1$-$C_4$haloalkyl, $C_1$-$C_4$alkoxy, $C_1$-$C_4$haloalkoxy, $CO_2$ or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, $C_3$-$C_{12}$cycloalkyl optionally substituted with one or more halogen, hydroxy, $C_1$-$C_4$alkoxy, ($C_1$-$C_4$alkyl)$SO_x$, $CONR_7R_8$, $CO_2R_9$, $R_{10}$, $R_{11}$, $C_3$-$C_6$cycloalkyl optionally substituted with one or three halogen, $C_1$-$C_4$alkyl, $C_1$-$C_4$haloalkyl, $C_1$-$C_4$alkoxy, $C_1$-$C_4$haloalkoxy, $NO_2$, or CN groups, phenyl optionally substituted with one or more halogen, $C_1$-$C_4$alkyl, $C_1$-$C_4$haloalkyl, $C_1$-$C_4$alkoxy, $C_1$-$C_4$haloalkoxy, $CO_2$or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups or $R_2$ and $R_3$ may be taken together to form a ring represented by the structure $$\begin{array}{c} \quad\quad(CH_2)_p \\ \quad\quad\diagup\quad\quad\diagdown \\ N \quad\quad\quad\quad X_r; \\ \quad\quad\diagdown\quad\quad\diagup \\ \quad\quad(CH_2)_m \end{array}$$

$R_4$, $R_5$ and $R_6$ are each independently hydrogen, halogen, CN, $NO_2$, ($C_1$-$C_4$alkyl)$SO_x$, ($C_1$-$C_4$haloalkyl)$SO_x$, $C_1$-$C_6$alkyl, $C_1$-$C_6$haloalkyl, $C_1$-$C_6$alkoxy or $C_1$-$C_6$haloalkoxy;

$R_7$, $R_8$ and $R_9$ are each independently hydrogen or $C_1$-$C_4$alkyl;

$R_{10}$ is $NR_{12}R_{13}$, $$\begin{array}{ccc} \quad(CH_2)_p & & \quad(CH_2)_p \\ \diagup\quad\diagdown & & \diagup\quad\diagdown \\ N\quad\quad\quad X_r & or\;\; CH\quad\quad X_r; \\ \diagdown\quad\diagup & & \diagdown\quad\diagup \\ \quad(CH_2)_m & & \quad(CH_2)_m \end{array}$$

$R_{11}$ is

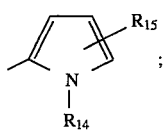

$R_{12}$, $R_{13}$, $R_{14}$ and $R_{15}$ are each independently hydrogen or $C_1$-$C_4$alkyl;

X is O, S or $NR_{14}$;

r is an integer of 0 to 1;

p and m are each independently an integer of 0, 1 2 or 3 with the provisos that only one of p, m or r can be 0 and that the sum of p+m+r must be 4, 5 or 6;

x is an integer of 0, 1 or 2; or the acid addition salts thereof.

The present invention further provides N-arylamidrazone compounds of formula I wherein A, B, W, Y, n R, $R_1$, $R_2$, and $R_3$ are as described hereinabove with the proviso that when all of A, B and W are other than N, then R and one of $R_2$ and $R_3$ are as described hereinabove with the proviso that when all of A, B and W are other than N, then R and one of $R_2$ or $R_3$ must be other than hydrogen and with the further proviso that when one of A, B or W is N, then Y, $R_4$, $R_5$ and $R_6$ must be other than $C_1$-$C_{10}$alkyl.

Compositions and methods for the protection of growing plants from attack and infestation by insects and acarina are also provide.

DETAILED DESCRIPTION OF THE INVENTION

A variety of insects and acarina cause great economic loss by damaging or destroying agricultural crops and other valuable plants; by aiding in the spread and development of bacteria, fungi and viruses that produce diseases of plants; and by destroying or lowering the value of stored foods, other products and possessions. Insects and acarina present some of the farmers' greatest problems the world over. The need for alternative and effective insect and acarid control is a global concern.

It has now been found that the substituted acid amide, N-arylhydrazone compounds of formula I are especially efficacious insecticidal and acaricidal agents, particularly against Colepotera, Lepidoptera and Acarina.

The formula I amidrazone compounds of the present invention have the structural formula

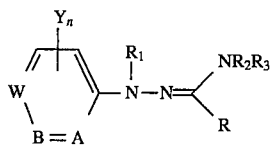

(I)

wherein A, B, W, Y, n R, $R_1$, $R_2$ and $R_3$ are described hereinabove. The term halogen as used in the specification and claims designates chlorine, fluorine, bromine or iodine. The term acid addition salts designates those salts formed by acids commonly known in the art such as hydrogen chloride, hydrogen bromide, hydrogen bisulfate, semi-hydrogen sulfate and the like. In the above definition when N is O then Y is hydrogen.

Preferred compounds of the invention are those wherein R, $R_2$ and $R_3$ are each independently hydrogen or $C_1$-$C_6$alkyl, A is C-$R_4$, B is C-$R_5$, W is C-$R_6$, Y is halogen and n is 1. Particularly preferred compounds are those wherein $R_1$ is hydrogen, $R_4$ is halogen, $R_5$ is hydrogen and/or $R_6$ is $C_1$-$C_6$alkyl substituted with one or more halogens, preferably trifluoromethyl.

Other preferred compounds of the invention are compounds having the structure

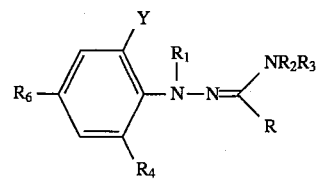

wherein R is $C_1$-$C_{10}$alkyl;

$R_1$ is hydrogen or $C_1$-$C_4$alkyl;

$R_2$ is $C_1$-$C_{10}$alkyl;

$R_3$ is hydrogen or $C_1$-$C_{10}$alkyl; and $R_4$, $R_6$ and Y are each independently hydrogen, halogen, CN, $NO_2$, hydrogen, halogen, CN, $NO_2$, $C_1$-$C_6$alkyl, $C_1$-$C_6$haloalkyl, $C_1$-$C_6$alkoxy, or $C_1$-$C_6$haloalkoxy.

The N-arylamidrazones of formula I may be prepared by reacting an acid chloride, hydrozone (hydrazinoyl chloride) of formula II with an amine compound, $HNR_2R_3$, as shown in flow diagram I.

Flow Diagram I

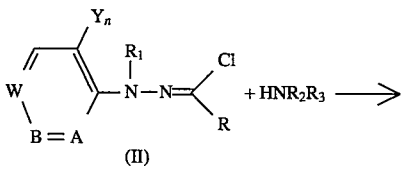

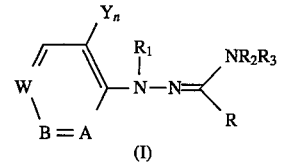

(I)

Compounds of formula II may be prepared by reacting a suitable arylhydrazine of formula III with the appropriate acid chloride, RCOCl, to obtain an N-arylhydrazine with a chlorinating agent such as thionyl chloride to give the desired formula II N-arylhydrozinoyl chloride product. The reaction is illustrated in flow diagram II.

Flow Diagram II

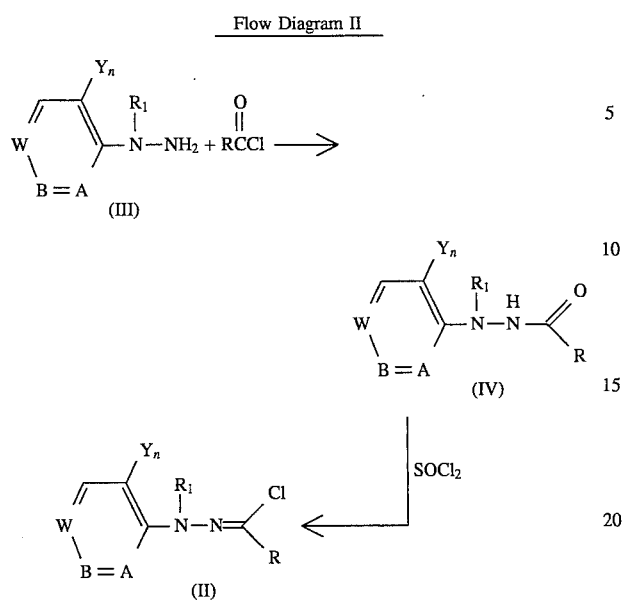

The substituted N-arylamidrazone compounds of the present invention are effective for controlling insect and acarid pests. Said compounds are also effective for protecting growing or harvested crops from attach and infestation by such pests.

In practice, generally about 10 ppm to 10,000 ppm, preferably about 100 to 5,000 ppm of the formula I compound dispersed in a liquid carrier, when applied to the plants or the soil or water in which they are growing, is effective to protect the plants from insect and acarina attack and infestation. Soil application of the formula I compounds is particularly effective for the control of the post-embryonic development stages of Coleoptera and Diptera. Applications, such as spray applications, of compositions of the invention are generally effective at rates which provide about 0.125 kg/ha to about 250 kg/ha, preferably about 10 kg/ha to 100 kg/ha. Of course, it is contemplated that higher or lower rates of application of the N-arylamidrazone compounds may be used dependent upon the

EXAMPLE 1

Preparation of 2,2-Dimethylpropionic acid,2-(2,6-dichloro-α,α,α-trifluoro-p-tolyl)hydraaide

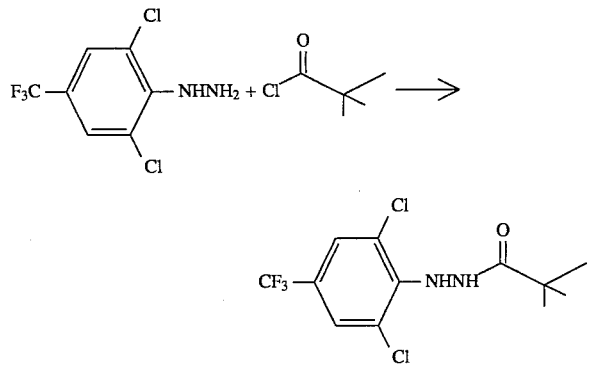

A solution of 2,6-dichloro-4-(trifluoromethyl)phenylhydrazine (50.0 g, 0.20 mol) in methylene chloride is treated dropwise with trimethylacetyle chloride (30.6 g, 0.254 mol), stirred for 30 minutes, treated with 10% aqueous NaOH and stirred for 3 hours. The phases are separated; the organic phase is washed with water, dried over $MgSO_4$ and concentrated in vacuo to give an off-white solid residue. The solid is recrystallized from 1,2-dichloroethane to give the title product as a white solid, 55 g (82% yield), mp 140°–141°, identified by $^1HNMR$, $^{13}CNMR$ and IR spectral analyses.

EXAMPLES 2–42

Preparation of substituted N-arylhydrazide derivatives

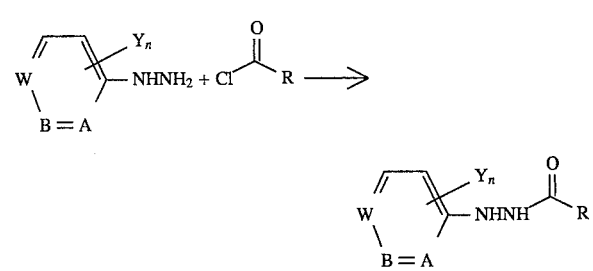

Using essentially the same procedure described above for Example 1 and substituting the appropriate arylhydrazine and acid chloride, the compounds shown in prevailing environmental circumstances such as population density, degree of infestation, stage of plant growth, solid conditions, weather conditions and the like.

Advantageously, the compounds of the invention may be used in conjunction with, or in combination with other biological and chemical control agents including other insecticides, nematicides, acaricides, molluscicides, fungicides and bactericides such as nuclear polyhedrosis viruses, pyrroles, arylpyrroles, halobenzoylureas, pyrethroids, carbamates, phosphates, and the like.

Typical formulations suitable for the formula I compounds of the invention are granular compositions, flowable compositions, wettable powders, dusts, microemulsions, emulsifiable concentrates and the like. All compositions which lend themselves to soil, water and foliage application and provide effective plant protection are suitable. Compositions of the invention include the formula I n-arylamidrazone amide compound admixed with an inert solid or liquid carrier.

where compositions of the invention are to be employed in combination treatments with other biological or chemical agents, the composition may be applied as an admixture of the components or may be applied sequentially.

For a more clear understanding of the invention, specific examples thereof are set forth below. These examples are merely illustrative, and are not to be understood as limiting the scope and underlying principles of the invention in any way.

Table I are prepared and identified by $^1HNMR$, $^{13}NMR$ and IR spectral analyses.

TABLE I

Structure: aryl-NHNH-C(=O)-R where the aryl ring contains B=A, W, and $Y_n$ substituents.

| Example Number | A | B | W | Yn | R | mp °C. |
|---|---|---|---|---|---|---|
| 2 | C—Cl | CH | C—CF₃ | 6-Cl | (CH₃)₂CHCH₂ | 135–136 |
| 3 | C—Cl | CH | C—Cl | 6-Cl | (CH₃)₃C | 124–125.5 |
| 4 | C—Cl | CH | CH | 6-Cl | (CH₃)₃C | 114–115 |
| 5 | C—Br | CH | C—CF₃ | 6-Br | (CH₃)₃C | 118–120 |
| 6 | C—Br | CH | C—CF₃ | 6-Br | CH₃ | 173–175 |
| 7 | C—Br | CH | C—CF₃ | 6-Br | C₆H₅ | 181–184 |
| 8 | C—CH₃ | CH | C—Cl | H | (CH₃)₃C | 103–106 |
| 9 | C—Cl | CH | C—CF₃ | 6-Cl | (CH₃)₃CCH₂ | 125–127 |
| 10 | C—Cl | CH | C—Cl | 6-Cl | pClC₆H₅ | 188–190 |
| 11 | C—Cl | CH | C—CF₃ | 6-Cl | (CH₃)₂CH | 158–159 |
| 12 | C—Cl | CH | C—Cl | 6-Cl | cyclopropyl | 186–188 |
| 13 | C—Cl | CH | C—CF₃ | 6-Cl | CH₃CH₂C(CH₃)₂ | 121–123 |
| 14 | C—H | CH | C—CF₃ | H | (CH₃)₃C | 136–139 |
| 15 | C—Cl | CH | C—CF₃ | H | (CH₃)₃C | 143–145 |
| 16 | C—Cl | CH | C—CF₃ | 6-Cl | norbornyl | 125–127 |
| 17 | C—Cl | C—Cl | C—Cl | 5,6-diCl | (CH₃)₃C | |
| 18 | N | CH | C—CF₃ | 6-Cl | (CH₃)₃C | 151–151.5 |
| 19 | C—Cl | CH | C—Cl | 6-Cl | 2,6-dichloro-4-(trifluoromethyl)phenyl hydrazide of pivalic acid | 138–140 |
| 20 | C—Cl | CH | C—CF₃ | 6-Cl | pClC₆H₅OC(CH₃)₂ | 137–139 |
| 21 | C—CF₃ | CH | CH | H | (CH₃)₃C | 98–100 |
| 22 | C—Cl | CH | C—CF₃ | 6-Cl | 1-methylcyclopropyl | 101–103 |
| 23 | C—Cl | CH | C—Cl | 6-Cl | cyclohexyl | 188–189 |
| 24 | C—Cl | CH | C—CF₃ | 6-Cl | C₆H₅C(CH₃)₂ | 104–105 |
| 25 | C—Cl | CH | C—Cl | 6-Cl | CF₃CF₂ | 131–132 |
| 26 | C—Cl | CH | C—Cl | 6-Cl | (CH₃)₂CH | 164–165 |
| 27 | C—Cl | CH | C—CF₃ | 6-Cl | cyclopropyl | 172–174 |
| 28 | C—Cl | CH | C—Cl | 6-Cl | CH₃CH₂C(CH₃)₂ | 132–134 |
| 29 | C—Cl | CH | C—CF₃ | 6-Cl | 1-adamantyl | 160–162 |
| 30 | C—Br | CH | C—CF₃ | 6-Br | (CH₃)₃C | 140–141 |
| 31 | C—Cl | CH | C—Cl | 6-Cl | CH₃(CH₂)₅C(CH₃)₂ | |
| 32 | N | N | C—Cl | H | (CH₃)₃C | 178–182 |
| 33 | C—Cl | CH | C—CF₃ | 6-Cl | 1-phenylcyclopropyl | 121–123 |
| 34 | C—Cl | CH | C—CF₃ | 6-Cl | pClC₆H₅C(CH₃)₂ | 105–107 |
| 35 | C—Cl | CH | C—CF₃ | 6-Cl | ClCH₂C(CH₃)₂ | 119–120 |
| 36 | C—Cl | CH | C—CF₃ | 6-Cl | 2,2-dichloro-1-methylcyclopropyl | 174–175 |

TABLE I-continued

|  |  |  | $Y_n$ |  |  |
|---|---|---|---|---|---|

(structure: W, B=A, Y_n, —NHNHC(=O)R)

| Example Number | A | B | W | Yn | R | mp °C. |
|---|---|---|---|---|---|---|
| 37 | C—Cl | CH | C—Cl | 6-Cl | ClCH$_2$C(CH$_3$)$_2$ | 124–125 |
| 38 | C—Cl | CH | CH | 5-CF$_3$ | (CH$_3$)$_3$C | 170–177.5 |
| 39 | C—Cl | CH | C—CF$_3$ | 6-Cl | 1-methylcyclohexyl | 105–107 |
| 40 | CH | C—CF$_3$ | CH | H | (CH$_3$)$_3$C | 158–160 |
| 41 | C—F | C—F | C—F | 5,6-diF | (CH$_3$)$_3$C | 154–157 |
| 42 | C—Br | CH | F | 6-Br | (CH$_3$)$_3$C | 118–120 |

EXAMPLE 43

Preparation of 1-chloro-2,2-dimethylpropionaldehyde, 2-(2,6-Dichloro-α,α,α-trifluoro-p-tolyl)hydrazone

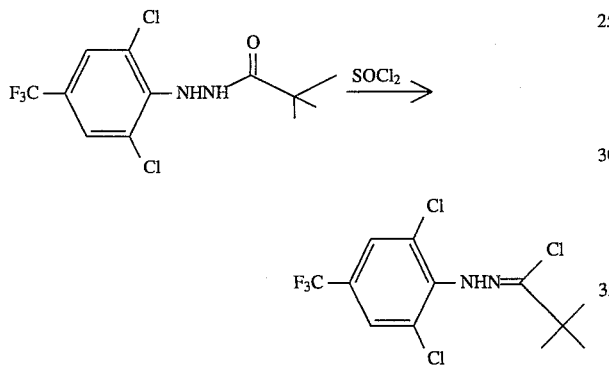

A mixture of 2,2-dimethyl-2-(2,6-dichloro-α,α,α-trifluoro-p-tolyl)hydrazide propionic acid (50.0 g, 0.152 mol) and thionyl chloride (53.8 g, 0.452 mol) in toluene is heated at reflux temperature for 8 hours, cooled to room temperature and concentrated in vacuo to give an oil residue. The oil is dissolved in hexanes and passed through a silica gel filter cake. The filtercake is washed with several portions of hexanes. The filtrates are combined and concentrated in vacuo to give the title product as a yellow oil, 47.2 g, (90% yield), identified by $^1$HNMR, $^{13}$CNMR and IR spectral analyses.

EXAMPLES 44–84

Preparation of substituted N-arylhydrazinoyl chlorides

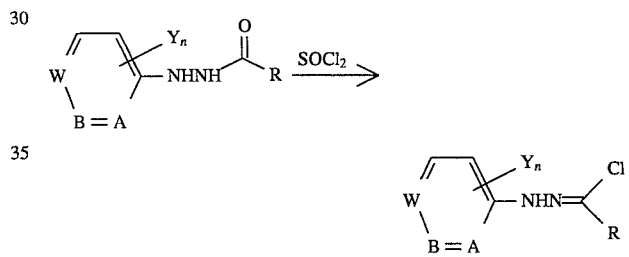

Using essentially the same procedure as described above in Example 43 and substituting the appropriate hydrazide substrate, the compounds shown in Table II are prepared and identified by $^1$NMR, $^{13}$CNMR and IR spectral analyses.

TABLE II

| Example Number | A | B | W | Yn | R | mp °C. |
|---|---|---|---|---|---|---|
| 44 | C—Cl | CH | C—CF$_3$ | 6-Cl | (CH$_3$)$_2$CHCH$_2$ |  |
| 45 | C—Cl | CH | C—Cl | 6-Cl | (CH$_3$)$_3$C | 44.5–45.5 |
| 46 | C—Cl | CH | CH | 6-Cl | (CH$_3$)$_3$C |  |
| 47 | C—Br | CH | C—F | 6-Br | (CH$_3$)$_3$C |  |
| 48 | C—Br | CH | C—CF$_3$ | 6-Br | CH$_3$ |  |
| 49 | C—Br | CH | C—CF$_3$ | 6-Br | C$_6$H$_5$ |  |
| 50 | C—CH$_3$ | CH | C—Cl | H | (CH$_3$)$_3$C |  |
| 51 | C—Cl | CH | C—CF$_3$ | 6-Cl | (CH$_3$)$_3$CCH$_2$ |  |
| 52 | C—Cl | CH | C—Cl | 6-Cl | pClC$_6$H$_5$ | 120 |
| 53 | C—Cl | CH | C—CF$_3$ | 6-Cl | (CH$_3$)$_2$CH |  |
| 54 | C—Cl | CH | C—Cl | 6-Cl | cyclopropyl |  |
| 55 | C—Cl | CH | C—CF$_3$ | 6-Cl | CH$_3$CH$_2$C(CH$_3$)$_2$ |  |
| 56 | C—H | CH | C—CF$_3$ | H | (CH$_3$)$_3$C |  |
| 57 | C—Cl | CH | C—CF$_3$ | H | (CH$_3$)$_3$C |  |

TABLE II-continued

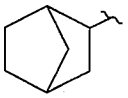

| Example Number | A | B | W | Yn | R | mp °C. |
|---|---|---|---|---|---|---|
| 58 | C—Cl | CH | C—CF$_3$ | 6-Cl | 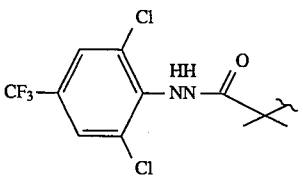 | |
| 59 | C—Cl | C—Cl | C—Cl | 5,6-diCl | (CH$_3$)$_3$C | |
| 60 | N | CH | C—CF$_3$ | 6-Cl | (CH$_3$)$_3$C | |
| 61 | C—Cl | CH | C—Cl | 6-Cl |  | |
| 62 | C—Cl | CH | C—CF$_3$ | 6-Cl | pClC$_6$H$_5$OC(CH$_3$)$_2$ | |
| 63 | C—CF$_3$ | CH | CH | H | (CH$_3$)$_3$C | |
| 64 | C—Cl | CH | C—CF$_3$ | 6-Cl | 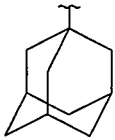 | |
| 65 | C—Cl | C—CH | C—Cl | 6-Cl | cyclohexyl | |
| 66 | C—Cl | C—CH | C—CF$_3$ | 6-Cl | C$_6$H$_5$C(CH$_3$)$_2$ | |
| 67 | C—Cl | CH | C—Cl | 6-Cl | CF$_3$CF$_2$ | |
| 68 | C—Cl | CH | C—Cl | 6-Cl | (CH$_3$)$_2$CH | |
| 69 | C—Cl | CH | C—CF$_3$ | 6-Cl | cyclopropyl | |
| 70 | C—Cl | CH | C—Cl | 6-Cl | CH$_3$CH$_2$C(CH$_3$)$_2$ | |
| 71 | C—Cl | CH | C—CF$_3$ | 6-Cl |  | 110–111 |
| 72 | C—Br | CH | C—CF$_3$ | 6-Br | (CH$_3$)$_3$C | |
| 73 | C—Cl | CH | C—Cl | 6-Cl | CH$_3$(CH$_2$)$_5$C(CH$_3$)$_2$ | |
| 74 | N | N | C—Cl | H | (CH$_3$)$_3$C | |
| 75 | C—Cl | CH | C—CF$_3$ | 6-Cl | 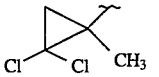 | |
| 76 | C—Cl | CH | C—CF$_3$ | 6-Cl | pClC$_6$H$_5$C(CH$_3$)$_2$ | 85–88 |
| 77 | C—Cl | CH | C—CF$_3$ | 6-Cl | ClCH$_2$C(CH$_3$)$_2$ | |
| 78 | C—Cl | CH | CCF$_3$ | 6-Cl |  | 71–73 |
| 79 | C—Cl | CH | C—Cl | 6-Cl | ClCH$_2$C(CH$_3$)$_2$ | |
| 79 | C—Cl | CH | C—Cl | 6-Cl | ClCH$_2$C(CH$_3$)$_2$ | |
| 80 | C—Cl | CH | CH | 5-CF$_3$ | (CH$_3$)$_3$C | |
| 81 | C—Cl | CH | C—CF$_3$ | 6-Cl | 1-methylcyclohexyl | |
| 82 | CH | C—CF$_3$ | CH | H | (CH$_3$)$_3$C | |
| 83 | CH | CH | CH | 5-F | (CH$_3$)$_3$C | |
| 84 | C—Br | CH | F | 6-Br | (CH$_3$)$_3$C | |

EXAMPLE 85

Preparation of N-Ethyl-2,2-dimethylpropionamide, 2-(2,6-Dichloro-α,α,α-trifluoro-p-tolyl)hydrazone 1-chloro-2,2-dimethylpropionaldehyde

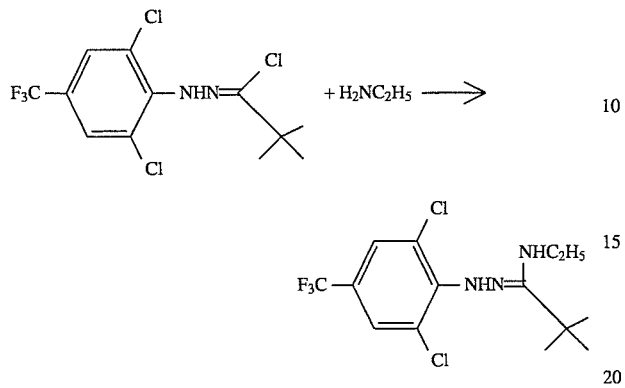

A solution of (2,6-dichloro-α,α,α-trifluoro-p-tolyl)hydrazone 1-chloro-2,2-dimethylpropionaldehyde (20.0 g, 0.575 mol) in tetrahydrofuran is treated dropwise with 70% aqueous ethylamine (28.0 g, 0.144 mol) at room temperature, stirred for 1 hour and concentrated in vacuo to give a semi-solid residue. The semi-solid is dispersed in ether and water. The phases are separated; the organic phase is washed with water, dried over MgSO$_4$ and concentrated in vacuo to give the title product as a yellow oil, 19.8 g (97% yield), identified by $^1$HNMR, $^{13}$CNMR and IR spectral analyses.

EXAMPLE 86–169

Preparation of substituted N-arylamidrazones

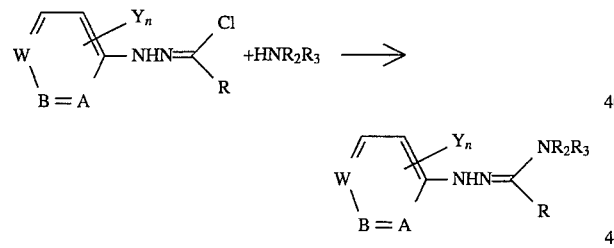

Using essentially the same procedure described above in Example 85 and substituting the appropriate hydrazinolychloride and a suitable amine, the compounds shown in Table III are prepared and identified by $^1$HNMR, $^{13}$CNMR and IR spectral analyses.

Hydrochloride salts of the invention may be prepared in accordance with the procedure outlined below.

EXAMPLE 146

Preparation of N-Ethyl-2,2-dimethylproprionamide, 2-(2,6-dichloro-α,α,α,-trifluoro-p-tolylhydrazone hydrochloride

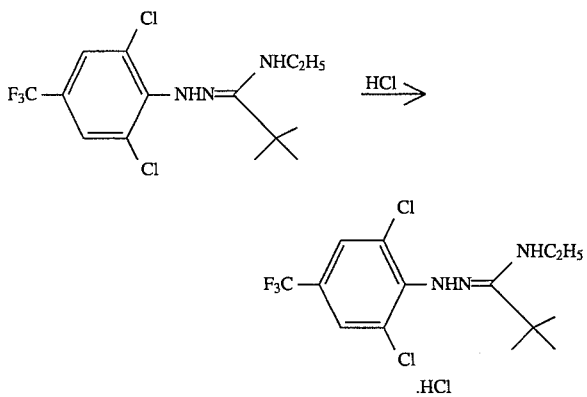

A stirred mixture of N-ethyl-2,2-dimethylpropionamide, 2(2,6-dichloro-α,α,α-trifluoro-p-tolylhydrazone (0.1 g, 2.8 mmol) and hexane is bubbled through with HCl gas for a 30 minute period. The resultant reaction mixture is filtered to give the title compound as a white solid, 1.13 g, mp 202°–202.5° C.

TABLE III

| Exmaple Number | A | B | W | Yn | R | R2 | R3 | mp °C. |
|---|---|---|---|---|---|---|---|---|
| 86 | C—Cl | CH | C—CF$_3$ | 6-Cl | (CH$_3$)$_3$C | pClC$_6$H$_5$ | H | |
| 87 | C—Cl | CH | C—Cl | 6-Cl | (CH$_3$)$_3$C | CH$_3$CH$_2$CH$_2$ | H | |
| 88 | C—Cl | CH | C—Cl | 6-Cl | (CH$_3$)$_2$CH | CH$_3$CH$_2$CH$_2$ | H | 48–50 |
| 89 | C—Cl | CH | C—CF$_3$ | 6-Cl | (CH$_3$)$_3$CCH$_2$ | CH$_3$CH$_2$CH$_2$ | H | |
| 90 | C—Cl | CH | C—Cl | 6-Cl | (CH$_3$)$_2$CH | cyclopropyl | H | |
| 91 | C—Cl | CH | C—CF$_3$ | 6-Cl | (CH$_3$)$_3$CCH$_2$ | CH$_3$CH$_2$ | H | |
| 92 | C—Cl | CH | C—CF$_3$ | 6-Cl | (CH$_3$)$_2$CH | CH$_3$CH$_2$ | H | 62–64 |
| 93 | C—Cl | CH | C—CF$_3$ | 6-Cl | (CH$_3$)$_3$C | CF$_3$CH$_2$ | H | |
| 94 | C—Br | CH | C—CF$_3$ | 6-Br | (CH$_3$)$_3$C | CH$_3$CH$_2$ | H | |
| 95 | C—Br | CH | C—CF$_3$ | 6-Br | (CH$_3$)$_3$C | CH$_3$CH$_2$CH$_2$ | H | |
| 96 | C—Br | CH | C—CF$_3$ | 6-Br | (CH$_3$)$_3$C | C$_6$H$_5$CH$_2$ | H | |
| 97 | C—Br | CH | C—CF$_3$ | 6-Br | (CH$_3$)$_3$C | furfuryl | H | |
| 98 | C—Br | CH | C—CF$_3$ | 6-Br | CH$_3$ | CH$_3$CH$_2$ | H | |

TABLE III-continued $$\text{structure with W, B=A, Y}^n\text{, NHN=C(R)NR}_2\text{R}_3$$

| Example Number | A | B | W | Yn | R | R2 | R3 | mp °C. |
|---|---|---|---|---|---|---|---|---|
| 99 | C—Br | CH | C—CF$_3$ | 6-Br | C$_6$H$_5$ | CH$_3$CH$_2$ | H | |
| 100 | C—Cl | CH | C—Cl | 6-Cl | (CH$_3$)$_3$C | H | H | 131–135 |
| 101 | C—Cl | CH | C—Cl | 6-Cl | (CH$_3$)$_3$C | CH$_3$ | CH$_3$ | 61–63 |
| 102 | C—Cl | CH | C—Cl | 6-Cl | (CH$_3$)$_3$C | CH$_3$CH$_2$ | H | |
| 103 | C—Cl | CH | C—CF$_3$ | H | (CH$_3$)$_3$C | CH$_3$CH$_2$CH$_2$ | H | |
| 104 | C—Cl | CH | CH | 6-Cl | (CH$_3$)$_3$C | CH$_3$CH$_2$CH$_2$ | H | |
| 105 | C—Cl | CH | C—CF$_3$ | 6-Cl | (CH$_3$)$_3$C | H | H | 100–102.5 |
| 106 | C—Cl | CH | C—CF$_3$ | 6-Cl | (CH$_3$)$_3$C | CH$_3$ | H | 78–79.5 |
| 107 | C—Cl | CH | C—CF$_3$ | 6-Cl | (CH$_3$)$_3$C | CH$_3$ | CH$_3$ | |
| 108 | C—Cl | CH | C—CF$_3$ | 6-Cl | (CH$_3$)$_3$C | CH$_3$CH$_2$ | H | |
| 109 | C—Cl | CH | C—CF$_3$ | 6-Cl | (CH$_3$)$_3$C | (CH$_3$)$_3$C | H | 67.5–68.5 |
| 110 | C—Cl | CH | C—CF$_3$ | 6-Cl | (CH$_3$)$_3$C | (CH$_3$)$_2$CHCH$_2$ | H | |
| 111 | C—Cl | CH | C—CF$_3$ | 6-Cl | (CH$_3$)$_3$C | —CH$_2$CH$_2$CH$_2$CH$_2$— | | |
| 112 | C—Cl | CH | C—Cl | 6-Cl | cyclopropyl | CH$_3$CH$_2$ | H | 65–67 |
| 113 | C—Cl | CH | C—CF$_3$ | 6-Cl | CH$_3$CH$_2$C(CH$_3$)$_2$ | CH$_3$CH$_2$ | H | |
| 114 | C—Br | CH | C—CF$_3$ | 6-Br | (CH$_3$)$_3$C | (CH$_3$)$_2$CH | H | |
| 115 | C—Cl | CH | C—CF$_3$ | H | (CH$_3$)$_3$C | —CH$_2$CH$_2$CH$_2$CH$_2$— | | |
| 116 | C—Cl | CH | C—CF$_3$ | 6-Cl | CH$_3$CH$_2$C(CH$_3$)$_2$ | CH$_2$CH$_2$ | CH$_3$CH$_2$ | |
| 117 | C—Cl | CH | C—CF$_3$ | H | (CH$_3$)$_3$C | CH$_3$CH$_2$ | H | |
| 118 | C—Cl | CH | C—Cl | 6-Cl | CH$_3$CH$_2$C(CH$_3$)$_2$ | CH$_3$CH$_2$ | H | |
| 119 | C—Cl | CH | C—CF$_3$ | 6-Cl | C$_6$H$_5$C(CH$_3$)$_2$ | CH$_3$CH$_2$ | H | |
| 120 | C—Cl | CH | C—CF$_3$ | H | (CH$_3$)$_3$C | —CH$_2$CH$_2$CH$_2$CH$_2$CH$_2$— | | |
| 121 | CH | CH | C—CF$_3$ | H | (CH$_3$)$_3$C | CH$_3$C$_2$ | H | |
| 122 | CH | CH | C—CF$_3$ | 6-Cl | (CH$_3$)$_2$CHCH$_2$ | CH$_3$CH$_2$ | H | 86.5 . 88.5 |
| 123 | C—Cl | CH | C—CF$_3$ | 6-Cl | (CH$_3$)$_3$C | —CH$_2$C$_2$CH$_2$CH$_2$CH$_2$— | | |
| 124 | C—Cl | CH | C—CF$_3$ | 6-Cl | (CH$_3$)$_3$C | cyclohexyl | H | |
| 125 | C—Cl | CH | C—CF$_3$ | 6-Cl | (CH$_3$)$_3$C | C$_6$H$_5$CH$_2$CH$_2$ | H | |
| 126 | C—Br | CH | C—F | 6-Br | (CH$_3$)$_3$C | CH$_3$CH$_2$ | H | |
| 127 | C—Cl | C—Cl | C—Cl | 5,6-diCl | (CH$_3$)$_3$C | CH$_3$CH$_2$ | H | 63–65 |
| 128 | C—Cl | CH | C—Cl | 6-Cl | CH$_3$(CH$_2$)$_5$C(CH$_3$)$_2$ | CH$_3$CH$_2$ | H | |
| 129 | C—Cl | CH | C—CF$_3$ | 6-Cl | adamantyl | CH$_3$CH$_2$ | H | |
| 130 | C—Cl | CH | C—CF$_3$ | 6-Cl | (CH$_3$)$_3$C | CH$_3$(CH$_2$)$_2$CH$_2$ | H | |
| 131 | C—Cl | CH | C—CF$_3$ | 6-Cl | (CH$_3$)$_3$C | (CH$_3$)$_2$CH | H | |
| 132 | C—Cl | CH | C—CF$_3$ | 6-Cl | (CH$_3$)$_3$C | 2-pyridyl-CH$_2$CH$_2$ | H | |
| 133 | C—Cl | CH | C—Cl | 6-Cl | pClC$_6$H$_5$ | (CH$_3$)$_2$CH | H | 124–127 |
| 134 | C—Cl | CH | C—Cl | 6-Cl | pCl$_6$H$_5$ | CH$_3$CH$_2$ | H | 127–132 |
| 135 | C—Cl | CH | C—CF$_3$ | 6-Cl | C$_6$H$_5$C(CH$_3$)$_2$ | C$_6$H$_5$CH$_2$CH$_2$ | H | |
| 136 | C—Cl | CH | C—CF$_3$ | 6-Cl | 1-methylcyclopropyl | CH$_3$CH$_2$ | H | 74–75 |
| 137 | C—CF$_3$ | CH | CH | H | (CH$_3$)$_3$C | CH$_3$CH$_2$ | H | |
| 138 | C—Cl | CH | C—CF$_3$ | H | (CH$_3$)$_3$C | C$_6$H$_5$CH$_2$CH$_2$ | H | |
| 139 | C—Cl | CH | C—CF$_3$ | H | (CH$_3$)$_3$C | 2-pyridyl-CH$_2$CH$_2$ | H | |
| 140 | CH | CH | C—CF$_3$ | H | (CH$_3$)$_3$C | 2-pyridyl-CH$_2$CH$_2$ | H | |
| 141 | C—Cl | CH | C—CF$_3$ | 6-Cl | pClC$_6$H$_5$C(CH$_3$)$_2$ | CH$_3$CH$_2$ | H | |
| 142 | C—Cl | CH | C—CF$_3$ | 6-Cl | (CH$_3$)$_3$C | C$_6$H$_5$CH(CH$_3$) | H | |

TABLE III-continued structure: W-B=A ring with NHN=C(R)(NR2R3), Y^n substituent

| Example Number | A | B | W | Y^n | R | R2 | R3 | mp °C. |
|---|---|---|---|---|---|---|---|---|
| 143 | C—Cl | CH | C—CF$_3$ | 6-Cl | (CH$_3$)$_3$C | (CH$_3$)$_2$NCH$_2$CH$_2$ | H | |
| 144 | C—Cl | CH | C—CF$_3$ | 6-Cl | (CH$_3$)$_3$C | CH$_3$CH$_2$C(CH$_3$)$_2$ | H | |
| 145 | C—Cl | CH | C—CF$_3$ | 6-Cl | (CH$_3$)$_3$C | 4-pyridyl-CH$_2$CH$_2$ | H | 100.5–101.5 |
| 146* | C—Cl | CH | C—CF$_3$ | 6-Cl | (CH$_3$)$_3$C | CH$_3$CH$_2$ | H | 202–202.5 |
| 147 | C—Br | CH | C—CF$_3$ | 6-Br | (CH$_3$)$_3$C | 2-pyridyl-CH$_2$CH$_2$ | H | |
| 148 | C—Cl | CH | C—CF$_3$ | 6-Cl | norbornyl | CH$_3$CH$_2$ | H | |
| 149 | C—Cl | CH | C—CF$_3$ | 6-Cl | 1-phenylcyclopropyl | CH$_3$CH$_2$ | H | |
| 150 | C—Cl | CH | C—CF$_3$ | 6-Cl | CH$_3$CH$_2$C(CCH$_3$)$_2$ | C$_6$H$_5$CH$_2$CH$_2$ | H | |
| 151 | C—Cl | CH | C—CF$_3$ | 6-Cl | (CH$_3$)$_3$C | C$_6$H$_5$CH$_2$ | H | |
| 152 | C—Cl | CH | C—CF$_3$ | 6-Cl | (CH$_3$)$_3$C | CH$_3$CH$_2$ | CH$_3$CH$_2$ | |
| 153 | C—Cl | CH | C—CF$_3$ | 6-Cl | 2,2-dichloro-1-methylcyclopropyl | CH$_3$CH$_2$ | H | |
| 154 | C—Cl | CH | C—CF$_3$ | 6-Cl | 2,2-dichloro-1-methylcyclopropyl | (CH$_3$)$_2$CH | H | |
| 155 | C—Cl | CH | C—CF$_3$ | 6-Cl | ClCH$_2$C(CH$_3$)$_2$ | pCF$_3$OC$_6$H$_5$ | H | 203–205 |
| 156 | C—Cl | CH | C—CF$_3$ | 6-Cl | (CH$_3$)$_3$C | neopentyl | H | |
| 157 | C—Cl | CH | C—CF$_3$ | 6-Cl | (CH$_3$)$_3$C | H$_2$NCOCCH(CH$_3$)$_2$ | H | 160–162 |
| 158 | C—Cl | CH | C—CF$_3$ | 6-Cl | (CH$_3$)$_3$C | piperidinyl-CH$_2$CH$_2$ | H | |
| 159 | C—Cl | CH | C—CF$_3$ | 6-Cl | (CH$_3$)$_3$C | pClC$_6$H$_5$—CH$_2$CH$_2$ | H | |
| 160 | C—Cl | CH | C—CF$_3$ | 6-Cl | (CH$_3$)$_3$C | (1-methylpyrrolyl)-CH$_2$CH$_2$ | H | |
| 161 | C—Cl | CH | C—CF$_3$ | 6-Cl | (CH$_3$)$_3$C | (1-methylpyrrolidinyl)-CH$_2$CH$_2$ | H | |
| 162 | C—Cl | CH | C—CF$_3$ | 6-Cl | (CH$_3$)$_3$C | CH$_3$(CH$_2$)$_4$CH(CH$_3$) | H | |
| 163 | C—Cl | CH | C—CF$_3$ | 6-Cl | (CH$_3$)$_3$C | CH$_3$(CH$_2$)$_4$CH(CH$_3$) | H | |
| 164 | C—Cl | CH | C—CF$_3$ | 6-Cl | (CH$_3$)$_3$C | CH$_2$=CHCH$_2$ | H | |
| 165 | C—Cl | CH | C—CF$_3$ | 6-Cl | 1-methylcyclohexyl | CH$_3$CH$_2$ | H | |
| 166 | C—Cl | CH | CH | 5-CF$_3$ | (CH$_3$)$_3$C | CH$_3$CH$_2$ | H | |
| 167 | C—F | C—F | C—F | 5,6-diF | (CH$_3$)$_3$C | CH$_3$CH$_2$ | H | |
| 168 | C—Br | CH | C—F | 6-Br | (CH$_3$)$_3$C | CH$_3$CH$_2$ | H | |

TABLE III-continued structure: W-B=A ring with Yn substituent, —NHN= linked to —C(R)=NR2R3

| Example Number | A | B | W | Yn | R | R2 | R3 | mp °C. |
|---|---|---|---|---|---|---|---|---|
| 169 | C—Cl | CH | C—CF₃ | 6-Cl | (CH₃)₃C | O(—CH₂CH₂—)N— (morpholine, N-attached via CH₂CH₂) | H | |

*Hydrochloride salt

EXAMPLE 170

Insecticidal and Acaricidal Evaluation of N-arylamidrazone compounds

Test solutions are prepared by dissolving the test compound in a 35% acetone in water mixture to give a concentration of 10,000 ppm. Subsequent dilutions are made with water as needed.

Spondoptera eridania, 3rd instar larvae, southern armyworm

A Sieva limabean leaf expanded to 7–8 cm in length is dipped in the test solution with agitation for 3 seconds and allowed to dry in a hood. The leaf is then placed in a 100×10 mm petri dish containing a damp filterpaper on the bottom and then 3rd instar caterpillars. At 3 and 5 days, observations are made of mortality, reduced feeding, or any interference with normal molting.

Tetranychus urticae(OP-resistant strain), 2-spotted spider mite

Sieva limabeam plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly mite-infested plants are dipped in the test solution for 3 seconds with agitation and set in the hood to dry. After 2 days, one leaf is removed and mortality counts are made. After 5 days, another leaf is removed and observations are made of mortality of the eggs and/or newly emerged nymphs.

Diabrotic undecimpunctata howardi, 3rd instar southern corn rootworm

One cc of fine talc is placed in a 30 ml wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, ten 3rd instar rootworms are added to each jar and the jars are loosely capped to allow air exchange for the larvae. The treatments are held for 6 days when mortality counts are made. Missing larvae are presumed dead, since they decompose rapidly and can not be found. The concentrations used in this test correspond approximately 50 kg/ha.

The data obtained are shown in Table IV.

TABLE IV

Insecticidal and Acaricidal Evaluation of N-Acrylamidrazones

| Compound (Ex. No.) | Armyworm[1] (300 ppm) % Mortality | 2-Spotted Mite[2] (300 ppm) % Mortality | Corn Rootworm[3] (50 kg/ha) % Mortality |
|---|---|---|---|
| 85 | 0 | 0 | 100 |
| 86 | 100 | 0 | 80 |
| 87 | 40 | 90 | 100 |
| 88 | — | — | — |
| 89 | 0 | 0 | 100 |
| 90 | 0 | 0 | 20 |
| 91 | 0 | 80 | 100 |
| 92 | 0 | 0 | 100 |
| 93 | 0 | 0 | 100 |
| 94 | — | 80 | 100 |
| 95 | 80 | 0 | 100 |
| 96 | 100 | 40 | 80 |
| 97 | 0 | 0 | 100 |
| 98 | 40 | 0 | 40 |
| 100 | 0 | 40 | 0 |
| 101 | 0 | 0 | 60 |
| 102 | 0 | 60 | 100 |
| 103 | 40 | 0 | 100 |
| 104 | 0 | 90 | 50 |
| 105 | 20 | 0 | 90 |
| 106 | 40 | 0 | 100 |
| 107 | — | — | 100 |
| 108 | 90 | 50 | 100 |
| 109 | 0 | 0 | 50 |
| 110 | 0 | 0 | 100 |
| 111 | 100 | 40 | 90 |
| 112 | 40 | 100 | 20 |
| 113 | 20 | 100 | 100 |
| 114 | 40 | 100 | 100 |
| 115 | 0 | 0 | 100 |
| 116 | 20 | 50 | 100 |
| 117 | 20 | 0 | 100 |
| 118 | 50 | 70 | 100 |
| 119 | 100 | 50 | 90 |
| 120 | — | 30 | 20 |
| 121 | 80 | 40 | 100 |
| 122 | 0 | 0 | 40 |
| 123 | 0 | 0 | 60 |
| 124 | 50 | 80 | 100 |
| 125 | 0 | 30 | 100 |
| 126 | 0 | 80 | 90 |
| 128 | 0 | 0 | 30 |
| 129 | 100 | 40 | 0 |
| 130 | 80 | 80 | 100 |
| 131 | 70 | 0 | 100 |

TABLE IV-continued

Insecticidal and Acaricidal Evaluation of N-Acrylamidrazones

| Compound (Ex. No.) | % Mortality | | |
|---|---|---|---|
|  | Armyworm[1] (300 ppm) | 2-Spotted Mite[2] (300 ppm) | Corn Rootworm[3] (50 kg/ha) |
| 132 | — | 40 | 100 |
| 133 | — | 0 | 0 |
| 134 | 0 | 30 | 0 |
| 135 | 0 | 0 | 0 |
| 136 | 0 | 70 | 100 |
| 137 | 0 | 0 | 100 |
| 138 | 0 | 0 | 100 |
| 139 | 0 | 70 | 100 |
| 140 | 0 | 0 | 50 |
| 141 | 100 | 0 | 0 |
| 142 | 0 | 0 | 100 |
| 143 | 0 | 0 | 100 |
| 144 | 0 | 0 | 100 |
| 145 | 0 | 0 | 100 |
| 146 | 0 | 0 | 100 |
| 147 | 0 | 0 | 100 |
| 148 | 50 | 0 | 100 |
| 149 | 100 | 80 | 80 |
| 150 | 0 | 60 | 100 |
| 152 | 80 | 0 | 100 |
| 153 | 100 | 0 | 100 |
| 156 | — | 0 | 100 |
| 157 | 0 | 0 | 100 |
| 158 | 40 | 0 | 100 |
| 159 | 0 | 0 | 100 |
| 160 | 0 | 0 | 100 |
| 161 | 0 | 0 | — |
| 162 | 0 | 100 | 100 |
| 163 | 0 | 0 | 100 |
| 164 | 0 | 0 | 100 |
| 167 | 0 | 0 | 100 |
| 168 | 0 | 80 | 90 |
| 169 | 0 | 0 | 100 |

[1]Armyworm is 3rd instar larvae, southern armyworm
[2]2-Spotted Mite is 2-spotted spider mite (OP-resistant)
[3]Corn Rootworm is 3rd instar southern corn rootworm

What is claimed is:

1. A method for the control of insect or acarid pests which comprises contacting said pests or their food supply, habitat or breeding grounds with a pesticidally effective amount of a compound having the structure

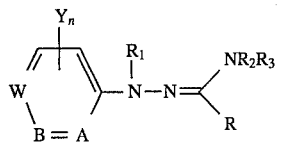

(I)

wherein

A is $C-R_4$ or N;

B is $C-R_5$ or N;

W is $C-R_6$ or N with the proviso that one and only one of A, B or W must be N;

Y is halogen, CN, $NO_2$, $C_1-C_6$alkyl, $C_1-C_6$haloalkyl, $C_1-C_6$alkoxy or $C_1-C_6$haloalkoxy;

n is an integer of 0, 1 or 2;

R is the hydrogen, $C_1-C_{10}$alkyl optionally substituted with one or more halogens, $C_3-C_6$cycloalkyl, $C_1-C_4$alkoxy, $C_1-C_4$haloalkoxy, $(C_1-C_4$alkyl$)SO_x$, $(C_1-C_4)SO_x$, phenyl optionally substituted with one to three halogen, $C_1-C_4$alkyl, $C_1-C_4$haloalkyl, $C_1-C_4$alkoxy, $C_1-C_4$haloalkoxy, $(C_1-C_4$alkyl$)SO_x$, $(C_1-C_4$haloalkyl$)SO_x$, $NO_2$ or CN groups, or phenoxy optionally substituted with one to three halogen, $C_1-C_4$alkyl, $C_1-C_4$haloalkyl, $C_1-C_4$alkoxy, $C_1-C_4$haloalkoxy, $(C_1-C_4$alkyl$)SO_x$, $(C_1-C_4$haloalkyl$)SO_x$, $NO_2$ or CN groups, $C_3-C_{12}$cycloalkyl optionally substituted with one or more halogens, $C_1-C_6$alkyl, $C_1-C_6$haloalkyl, $(C_1-C_4$alkyl$)SO_x$, $(C_1-C_4$haloalkyl$)SO_x$, phenyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups, or phenoxy optionally substituted with one to three halogen, $C_1-C_4$alkyl, $C_1-C_4$haloalkyl, $C_1-C_4$alkoxy, $C_1-C_4$haloalkoxy, $NO_2$ or CN groups, or phenyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups;

$R_1$ is hydrogen or $C_1-C_4$alkyl;

$R_2$ and $R_3$ are each independently hydrogen, $C_1-C_{10}$alkyl optionally substituted with one or more halogen, hydroxy, $C_1-C_4$alkoxy, $(C_1-C_4$alkyl$)SO_x$, $CONR_7R_8$, $CO_2R_9$, $R_{10}$, $C_3-C_6$cycloalkyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups, phenyl optionally substituted with one or more halogen, $C_1-C_4$alkyl, $C_1-C_4$haloalkyl, $C_1-C_4$alkoxy, $C_1-C_4$haloalkoxy, $CO_2$ or CN groups, or pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups, $C_3-C_{10}$alkenyl optionally substituted with one or more halogen, hydroxy, $C_1-C_4$alkoxy, $(C_1-C_4$alkyl$)SO_x$, $CONR_7R_8$, $CO_2R_9$, $R_{10}$, $C_3-C_6$cycloalkyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups, phenyl optionally substituted with one or more halogen, $C_1-C_4$alkyl, $C_1-C_4$haloalkyl, $C_1-C_4$alkoxy, $C_1-C_4$haloalkoxy, $CO_2$ or CN groups, or pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups, $C_3-C_{10}$alkenyl optionally substituted with one or more halogen, hydroxy, $C_1-C_4$alkoxy, $(C_1-C_4$alkyl$)SO_x$, $CONR_7R_8$, $CO_2R_9$, $R_{10}$, $C_3-C_6$cycloalkyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups, phenyl optionally substituted with one or more halogen, $C_1-C_4$alkyl, $C_1-C_4$haloalkyl, $C_1-C_4$alkoxy, $C_1-C_4$haloalkoxy, $CO_2$ or CN groups, or pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups, $C_3-C_{12}$cycloalkyl optionally substituted with one or more halogen, hydroxy, $C_1-C_4$alkoxy, $(C_1-C_4$alkyl$)SO_x$, $CONR_7R_8$, $CO_2R_9$, $R_{10}$, $C_3-C_6$cycloalkyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups, phenyl optionally substituted with one or more halogen, $C_1-C_4$alkyl, $C_1-C_4$haloalkyl, $C_1-C_4$alkoxy, $C_1-C_4$haloalkoxy, $CO_2$ or CN groups, or pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups;

$R_4$, $R_5$ and $R_6$ are each independently hydrogen, halogen, CN, $NO_2$, $(C_1-C_4$alkyl$)SO_x$, $(C_1-C_4$haloalkyl$)SO_x$, $C_1-C_6$alkyl, $C_1-C_6$haloalkyl, $C_1-C_6$alkoxy, or $C_1-C_6$haloalkoxy;

$R_7$, $R_8$ and $R_9$ are each independently hydrogen or $C_1$–$C_4$alkyl;

$R_{10}$ is $NR_{12}R_{13}$;

$R_{12}$ and $R_{13}$ are each independently hydrogen or $C_1$–$C_4$alkyl;

x is an integer of 0, 1 or 2; or the acid addition salts thereof.

2. The method according to claim 1 wherein R, $R_2$ and $R_3$ are each independently hydrogen or $C_1$–$C_{10}$ alkyl.

3. The method according to claim 1 wherein the insect pests are Coleoptera.

4. A method for the protection of growing plants from attack or infestation by insect or acarid pests which comprises applying to the foliage of the plants, or to the soil or water in which they are growing, a pesticidally effective amount of a compound having the structure:

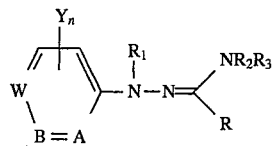 (I)

wherein A, B, W, Y, n, R, $R_1$, $R_2$ and $R_3$ are described in claim 1.

5. The method according to claim 4 wherein R, $R_2$ and $R_3$ are each independently hydrogen or $C_1$–$C_{10}$ alkyl.

6. The method according to claim 4 wherein the insect pests are Coleoptera.

7. The method according to claim 1 wherein A is N, B is CH, and W is $CCF_3$.

8. The method according to claim 4 wherein A is N, B is CH, and W is $CCF_3$.

9. A composition for controlling insect or acarid pests which comprises an inert liquid or solid carrier and a pesticidally effective amount of a compound having the structure

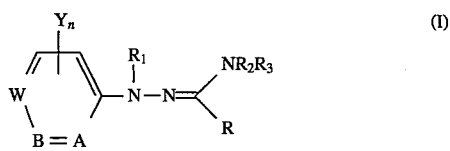 (I)

wherein A, B, W, Y, n, R, $R_1$, $R_2$ and $R_3$ are described in claim 1.

* * * * *